United States Patent [19]

Compton et al.

[11] Patent Number: 4,594,902

[45] Date of Patent: Jun. 17, 1986

[54] METHOD AND APPARATUS FOR SAMPLE RETRIEVAL FROM PHARMACEUTICAL DISSOLUTION TESTERS

[75] Inventors: Bruce J. Compton, Pittsford; Orville N. Hinsvark, Avon, both of N.Y.

[73] Assignee: Pennwalt Corporation, Philadelphia, Pa.

[21] Appl. No.: 768,596

[22] Filed: Aug. 23, 1985

[51] Int. Cl.⁴ .................................... G01N 1/00
[52] U.S. Cl. .......................... 73/863.23; 73/864.11
[58] Field of Search .......... 73/863.23, 863.24, 863.25, 73/863.01, 864, 864.11, 864.21, 864.24, 864.81, 864.86, 864.87

[56] References Cited

U.S. PATENT DOCUMENTS

| | | | |
|---|---|---|---|
| 3,490,288 | 1/1970 | Patnode | 73/863.23 |
| 3,550,453 | 12/1970 | Lightner et al. | 73/864.21 |
| 3,795,149 | 3/1974 | Gillette et al. | 73/863.24 |
| 4,046,593 | 9/1977 | Au et al. | 73/863.23 |
| 4,120,662 | 10/1978 | Fosslien | 73/864.24 |
| 4,325,909 | 4/1982 | Coulter et al. | 73/864.24 |
| 4,478,095 | 10/1984 | Bradley et al. | 73/864.21 |
| 4,501,164 | 2/1985 | Stockdale et al. | 73/864.21 |

FOREIGN PATENT DOCUMENTS 2084319 4/1982 United Kingdom ............ 73/864.24

Primary Examiner—Stewart J. Levy
Assistant Examiner—Robert R. Raevis

[57] ABSTRACT

Discrete robotic sampling apparatus for withdrawing samples of pharmaceutical formulations having particulates therein contained within a plurality of dissolution vessels. The apparatus employs a single sampling probe utilizing a single in-line filter therein. Movement of the probe is guided by a robotic arm controlled by a programmable microprocessor which also controls a reversible pump for flushing the particulates retained by the filter, by means of filtered sample, back into the dissolution vessel, prior to dispensing a portion of the filtered sample into a sample container. The probe is then programmed to be washed with a wash solution prior to inserting of the probe into another dissolution vessel for withdrawing of sample therefrom.

8 Claims, 3 Drawing Figures

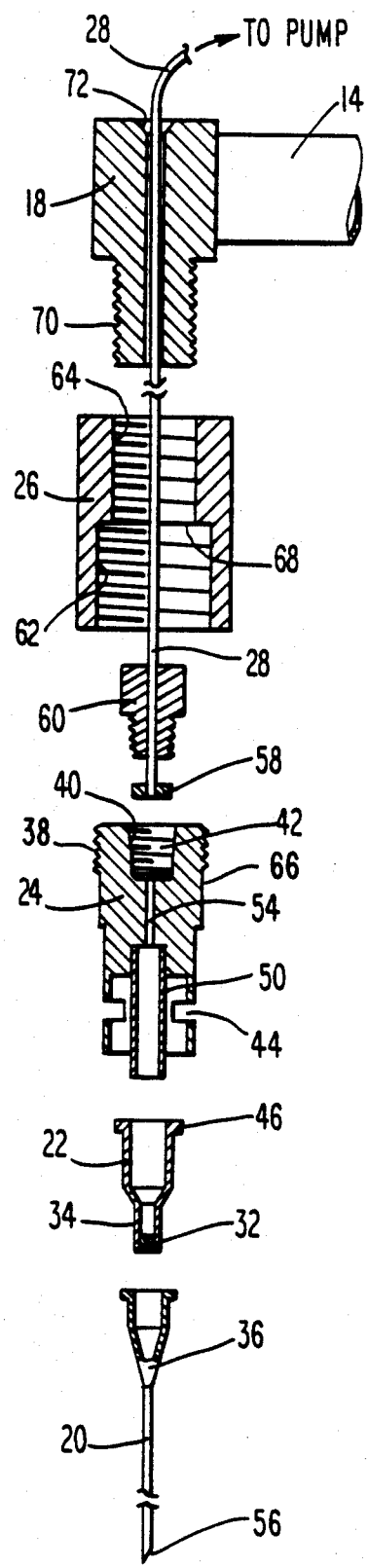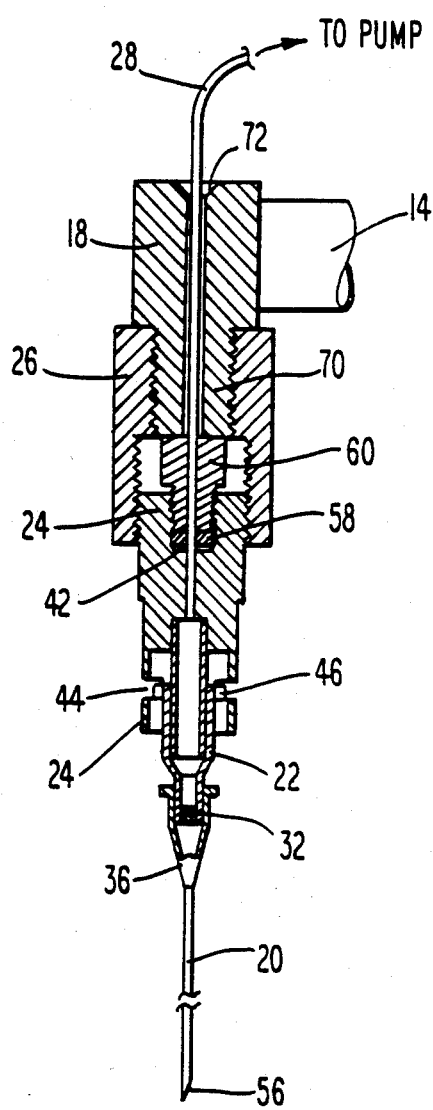
Fig. 2
Fig. 3

METHOD AND APPARATUS FOR SAMPLE RETRIEVAL FROM PHARMACEUTICAL DISSOLUTION TESTERS

STATEMENT OF THE INVENTION

This invention relates to dissolution testing and more particularly to discrete robotic sampling apparatus which is reliable and economical in operation while permitting faster sampling retrievals and rates from a plurality of dissolution vessels, and improved methods of retrieving samples from the dissolution vessels.

BACKGROUND AND SUMMARY OF THE INVENTION

One means of studying the in vitro release rate of drug substances from pharmaceutical formulations into simulated biological fluids is by dissolution testing. This type of testing is of particular importance in the study of sustained release formulations where drug release rates must be carefully controlled. Existing means for automating this type of testing includes the use of apparatus designed to sample from the dissolution vessels continuously or discretely.

In the continuous sampling from dissolution vessels, a single probe per dissolution vessel is employed. An in-line filter assures the absence of particulates being sampled. Since the sample is drawn in a more or less continuous fashion, clogging of the filter comprises a drawback in this type of operation.

Discrete sampling is normally accomplished using apparatus which incorporates a disposable tip filter removably affixed to the end of the sampling probe. The filter element is changed before sample is retrieved from another dissolution vessel in order to guard against the carrying over of any sample. Thus, filter clogging is not a concern in the discrete type of sampling as in the continuous type aforediscussed. A limitation of the discrete sampling method however is the need to change tip filters before sample retrieval from different dissolution vessels.

Automated dissolution sampling apparatus are commercially available from Zymark Corporation of Hopkinton, Mass., for example, and Van-Kel Industries of Edison, N.J., among others. The commercial automatic samplers often include arms or extensions performing sampling operations in a sequence governed by microprocessor controlled robotics, as in the present invention. Existing automated sampling apparatus however does not permit a single in-line filter and a single probe to sample from a plurality of dissolution vessels.

The present invention provides a discrete robotic sampling apparatus which employs a single in-line filter for ease of operation, while requiring but a single probe for sampling from a plurality of dissolution vessels. The single in-line filter and single probe of the present apparatus have been successfully and repeatedly used for retrieving samples from as many as 24 dissolution vessels over a time period extending beyond 24 hours.

The apparatus employs a reversible pump programmed to pull several milliliters of sample from a dissolution vessel through the hypodermic needle and in-line filter of the probe. The pump is then reversed to force filtered sample through the filter in the reverse direction to clear it of particulate matter retained by the filter. Backflushing of the filter eliminates clogging thereof and the possibility of transferring particulates to the sample container. By backflushing with the filtered sample rather than with external fluid, the need for additional valves and means for controlling the valves is eliminated as well as permitting faster sampling rates.

The apparatus is also provided with a clean-out mode between sample retrievals from different dissolution vessels to insure an absence of residual portions of an older sample from mixing with or being carried over to successive samples.

BRIEF DESCRIPTION OF THE DRAWINGS

FIG. 2 is an exploded sectional view of the sampling probe of FIG. 1.

FIG. 3 is a longitudinal sectional view of the sampling probe of FIG. 2 in assembled form.

DETAILED DESCRIPTION OF THE INVENTION

Figure 1:
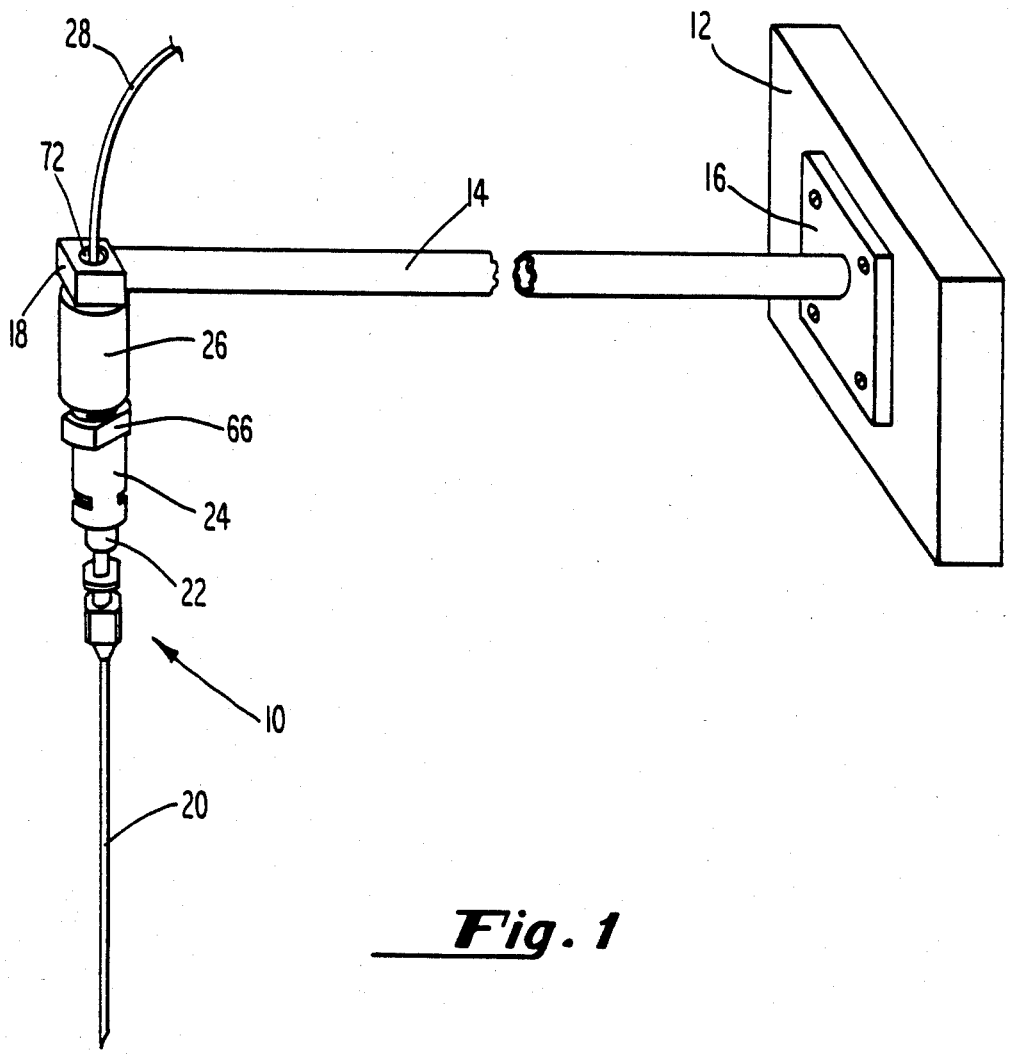
FIG. 1 is a perspective view of the improved sampling apparatus of the present invention.

In FIG. 1, a sampling probe 10 moves in response to movement of a blank hand 12 through a robotic arm or extension 14 articulating therebetween. Arm 14 has one end affixed to a plate 16 which may be threadedly mounted to blank hand 12, and threadedly receives or is otherwise secured to arm connector 18 of probe 10 at its other end. Arm connector 18, of course, can be made integral with the robotic arm.

Blank hand 12 is commercially available, suitably a Model Z920, for example, manufactured by Zymate Corporation of Hopkinton, MA, and was designed for attaching laboratory devices such as measurement probes used in automated procedure. Blank hand 12 is controlled by a suitable commercially available laboratory robot (not shown), typically a Zymate 100 System which includes microprocessing means for programming movements of the blank hand through the laboratory robot. Laboratory robotic devices controlled by microprocessors are well known and are not shown or further described herein.

Probe 10 further includes an hypodermic needle 20 through which the sample is withdrawn from a dissolution vessel (not shown). The dissolution vessel is partially immersed in a suitable water bath which permits the temperature inside the vessel to be maintained at about 37° C. during the test while being stirred, as described in *The United States Pharmacopeia*, 21st Revision, Jan. 1, 1985. A filter housing 22, a Luer lock connector 24, and a probe hub connector 26 are further illustrated in FIG. 1, each of these named components being disposed successively downstream the hypodermic needle 20 in the order mentioned.

Probe hub connector 26 is threadedly mounted to arm connector 18. Connection tubing 28 communicates with hypodermic needle 20, described more fully hereinafter.

Referring now to FIGS. 2 and 3 of the drawings, filter housing 22, typically plastic, includes a filter element 32 confined within a lower portion 34. Filter element 32 may be sintered polypropylene having a nominal pore size of 50 microns. Lower portion 34 of filter housing 22 is friction fitted into chamber 36 provided at the downstream or coupling end of hypodermic needle 20.

Upper portions of Luer lock connector 24 are exteriorly threaded at 38 and interiorly threaded at 40, the latter defining a cavity 42. Connector 24 is provided with a pair of opposed lateral slots 44 at its lower portion which receives flanged members 46 provided uppermost on filter housing 22 for interlocking the two members.

Luer lock connector 24 is provided with an axially disposed nozzle member 50 which extends therebelow for engaging filter housing 22 when it is in locked relationship to the Luer lock connector 24. An axial passageway 54 is provided within Luer lock connector 24 between cavity 42 and nozzle member 50 permitting communication between the tip end 56 of the needle to cavity 42.

Seated within cavity 42 is an orificed terminal ferrule 58 which is secured to the upstream end of connection tubing 28. An orificed compression nut 60 is threadedly received within cavity 42. Probe hub connector 26 includes a pair of interiorly threaded axial bores, a larger lower bore 62 and a smaller upper bore 64. Lower bore 62 threadedly receives exteriorly threaded portion 38 of Luer lock connector 24 which is provided with a pair of opposed flats 66 (FIG. 1) for engagement by a suitable wrench, if needed, in order to further turn the Luer lock connector 24 into the probe hub connector 26 to thereby compress nut 60 against annular shoulder 68 formed in hub connector 26 by means of the difference in diameters between bores 62 and 64.

Arm connector 18 is necked down to form an exteriorly threaded stud 70 at a lower portion thereof for reception within bore 64 of probe hub connector 26. A continuous axial passageway 72 is provided within arm connector 18 and stud 70 through which passageway the connection tubing 28 passes. It is apparent therefore that direct communication exists between tip 56 of needle 20 and the downstream end of connection tubing 28 extending beyond passageway 72 in arm connector 18.

Tubing 28 is connected to reversible pump means, typically a syringe pump (not shown) at its exteriorly disposed or downstream end. The syringe pump is microprocessor controlled and programmed to withdraw sample from the dissolution vessel or to urge filtered sample to flow back through the filter element 32. Connection tubing 28 should be of sufficient length in order to store at least 10 ml of the filtered sample therein.

In operation, the robotic arm or extension 14, responsive to movements of blank hand 12 controlled and programmed by the microprocessor unit, causes needle 20, typically 17 gauge and 3½ inches long, to be inserted into a dissolution vessel for withdrawal of, let's say, 6 to 7 ml of sample into connection tubing 28 by means of the reversible syringe pump. The sample is pulled through filter element 32 before being stored in the connection tubing.

The syringe pump now causes a fraction of the filtered sample, at least 2 ml thereof, to be pushed back through the in-line filter and hypodermic probe needle into the sample dissolution vessel to thereby adequately backflush the filter element of particulates retained thereon.

The robotic arm next places the probe 10 over a container (not shown) in which the sample is to be stored. The sample container may be protected by a septa which is readily punctured by needle 20 resulting in a cleaning of the needle's exterior.

After the desired amount of filtered sample, typically about ½ to 4½ ml, is dispensed into the sample container by the programmed syringe pump, robotic arm 14 moves probe 10 over a waste container (not shown) in order that any remaining sample in the probe or connection tubing is purged by means of the pump. The pump is then programmed to force at least 10 ml of a suitable wash solution from an external source through the connection tubing and probe prior to immersion of the needle into another dissolution vessel for withdrawal of sample therefrom.

An alternative sampling method employs a sampling valve in the connection tubing external the probe in order that filtered sample may be introduced to a liquid chromatographic system or flow injection analyzer, thus permitting real time analysis of dissolution samples and the simultaneous storing of filtered samples for other desired analyses.

It is apparent from the above description that improved apparatus and methods are provided by the present invention which permit a single probe having a single in-line filter associated therewith to quickly, reliably and economically withdraw samples for analysis from a plurality of dissolution vessels.

We claim:

1. Apparatus for retrieving samples from a vessel containing a formulation with suspended particulates therein, said apparatus including a robotic arm controlled by programmable microprocessor means for guiding a sampling probe depending from an outer end portion of said robotic arm, the improvement to said apparatus wherein samples are discretely retrieved from a plurality of such vessels by a single sampling probe having a single in-line filter therein, said probe comprising
   an hypodermic needle at a lower end of said probe for withdrawing sample from said vessel,
   a single filter member downstream said needle and communicating therewith for filtering said particulates from said withdrawn sample to provide filtered sample,
   connecting means downstream said filter member for locking said filter member into fixed position in said probe while permitting communication between said filter member and said connecting means,
   tubing means in communicating relationship with said connecting means, said tubing means connected externally said probe to reversible pump means controlled by said programmable microprocessor, said pump means causing said formulation to be withdrawm through said needle and filter member to provide said filtered sample downstream said filter member to be stored in said tubing means, and said particulates to be retained upstream said filter member, said pump means being programmed to cause said filtered sample to reverse its direction of flow to dislodge said retained particulates back into said vessel,
   other means for dispensing said filtered sample stored in said tubing means into a sample container, and
   additional means for cleaning said probe prior to insertion of said probe into another vessel for retrieving samples therefrom.

2. Apparatus of claim 1 wherein said additional means includes means for disposing of said filtered sample not dispensed into said sampling container into a waste container.

3. Apparatus of claim 1 further characterized by
   a hub connector mounted to said connecting means downstream thereof,
   an arm connector mounted to said hub connector downstream thereof and to an outer portion of said robotic arm, said hub connector and arm connector each having axial passageways for passage of said tubing means therethrough.

4. Apparatus of claim 3 wherein said arm connector is integrally formed to outer portion of said robotic arm.

5. Apparatus of claim 3 wherein said axial passageways in said hub connector comprise a pair of different diameter threaded bores forming a shoulder therebetween, said connecting means having exteriorly threaded and interiorly threaded upper portions, said interiorly threaded upper portion forming a cavity, a compression nut exteriorly threaded at a lower portion for threaded reception within said cavity of said connecting means, upper portion of said compression nut abutting said shoulder of said hub connector when exteriorly threaded portion of said connecting means is threadedly mounted within lower of said threaded bores of said hub connector, and means for securing said tubing means within said cavity of said connecting means whereby communication is provided between said needle and said pump means.

6. In a method of employing apparatus for automatically retrieving samples from a plurality of dissolution vessels containing pharmaceutical formulations with suspended particulates therein by means of a probe depending from a robotic arm extending from a blank hand controlled by programmable microprocessor means, the improvement to said method wherein a filter backflushing step and a probe clean-out step permit said apparatus to require but a single in-line filter and a single probe with an attached hypodermic needle respectively for retrieving said samples from said plurality of dissolution vessels within a limited time period, said method comprising the steps of placing the hypodermic needle of said probe into dissolution vessel containing said formulation to be sampled, withdrawing a portion of said formulation through said hypodermic needle and filter of said probe to provide filtered sample downstream said filter and particulates upstream thereof, storing said filtered sample in tubing downstream said filter, said tubing communicating with said filter, backflushing said filter to release said particulates back into said dissolution vessel, placing said probe over a sample container for dispensing a desired amount of said filtered sample therein, placing said probe over a waste container for dispensing reamining filtered sample therein, pumping wash solution through said probe to clear any remaining sample therefrom, and returning said cleared probe over another dissolution vessel for retrieval of sample therefrom.

7. The method of claim 6 wherein said sampling container is protected by a septa and said step of placing said probe over a sample container includes puncturing said septa with said probe needle.

8. The method of claim 7 wherein said puncturing step aids in cleaning exterior of said needle.

* * * * *